(12) United States Patent
Mansfield et al.

(10) Patent No.: US 11,812,932 B2
(45) Date of Patent: Nov. 14, 2023

(54) GUIDEWIRE LOCKING DEVICE

(71) Applicant: Olympus Corporation, Tokyo (JP)

(72) Inventors: Richard P. Mansfield, Sterling, MA (US); Michael J. Perriello, Hopedale, MA (US); Andy K. Khin, Lowell, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 1003 days.

(21) Appl. No.: 16/161,227

(22) Filed: Oct. 16, 2018

(65) Prior Publication Data

US 2020/0114127 A1 Apr. 16, 2020

(51) Int. Cl.
*A61B 1/018* (2006.01)
*A61M 25/09* (2006.01)
*A61B 1/00* (2006.01)

(52) U.S. Cl.
CPC .......... *A61B 1/018* (2013.01); *A61B 1/00147* (2013.01); *A61M 25/09* (2013.01); *A61M 2025/09125* (2013.01)

(58) Field of Classification Search
CPC ........ A61M 25/09; A61M 2025/09125; A61M 25/09041; A61B 1/00147; A61B 1/00131; A61B 1/01; A61B 1/018
See application file for complete search history.

(56) References Cited

U.S. PATENT DOCUMENTS

| | | | |
|---|---|---|---|
| 6,096,009 A | 8/2000 | Windheuser et al. | |
| 6,533,772 B1 * | 3/2003 | Sherts | A61M 25/0113 279/42 |
| 6,893,393 B2 | 5/2005 | Carrillo | |
| 7,637,863 B2 | 12/2009 | Deal et al. | |
| 7,803,107 B2 | 9/2010 | Carrillo | |
| 7,967,830 B2 | 6/2011 | Ayala et al. | |
| 8,025,629 B2 | 9/2011 | Shelton | |
| 8,206,320 B2 | 6/2012 | Deal et al. | |
| 8,211,087 B2 | 7/2012 | Carter et al. | |
| 8,512,389 B2 | 8/2013 | Ayala et al. | |
| 8,591,563 B2 | 11/2013 | Karpiel et al. | |

(Continued)

FOREIGN PATENT DOCUMENTS

| | | |
|---|---|---|
| CN | 105816208 B | 8/2018 |
| CN | 112911984 A | 6/2021 |

(Continued)

OTHER PUBLICATIONS

"U.S. Appl. No. 16/163,828, Preliminary Amendment filed Jan. 22, 2020", 3 pgs.

(Continued)

*Primary Examiner* — Sean P Dougherty
(74) *Attorney, Agent, or Firm* — Schwegman Lundberg & Woessner, P.A.

(57) ABSTRACT

A device that includes a body, a wire locking feature, and a channel. The body has an opening through which a wire is configured to extend. The channel is defined by an upper wire guiding portion and a lower wire guiding portion. The channel is configured to guide the wire between the opening and the wire locking feature. The upper wire guiding portion includes a protrusion. The wire is configured to slip past the protrusion during insertion of the wire into the channel.

14 Claims, 7 Drawing Sheets

(56) References Cited

U.S. PATENT DOCUMENTS

| | | | |
|---|---|---|---|
| 8,647,256 | B2 | 2/2014 | Carrillo, Jr. |
| 10,238,845 | B2* | 3/2019 | Ha .................... A61M 25/0113 |
| 10,674,894 | B2* | 6/2020 | Khanicheh ............ A61B 1/018 |
| 2004/0162465 | A1 | 8/2004 | Carrillo |
| 2005/0075647 | A1 | 4/2005 | Walters et al. |
| 2006/0195117 | A1 | 8/2006 | Rucker et al. |
| 2012/0323146 | A1* | 12/2012 | Eden .................... A61B 1/012 |
| | | | 600/585 |
| 2014/0100552 | A1 | 4/2014 | Gallacher et al. |
| 2017/0319828 | A1 | 11/2017 | Doepker et al. |
| 2020/0121897 | A1 | 4/2020 | Mansfield et al. |

FOREIGN PATENT DOCUMENTS

| | | |
|---|---|---|
| JP | 2022505180 A | 1/2022 |
| WO | WO-2017183366 A1 | 10/2017 |
| WO | WO-2020081440 A1 | 4/2020 |

OTHER PUBLICATIONS

"International Application Serial No. PCT/US2019/056090, International Preliminary Report on Patentability dated Apr. 29, 2021", 9 pgs.

"International Application Serial No. PCT/US2019/056090, International Search Report dated Jan. 30, 2020", 5 pgs.

"International Application Serial No. PCT/US2019/056090, Written Opinion dated Jan. 30, 2020", 9 pgs.

"U.S. Appl. No. 16/163,828, Final Office Action dated Apr. 4, 2022", 7 pgs.

"U.S. Appl. No. 16/163,828, Non Final Office Action dated Dec. 2, 2021", 11 pgs.

"U.S. Appl. No. 16/163,828, Response filed Feb. 17, 2022 to Non Final Office Action dated Dec. 2, 2021", 9 pgs.

"European Application Serial No. 19798770.4, Notification to Correct Deficiency in the Amendments Rule 137(4) dated Mar. 18, 2022", 2 pgs.

"U.S. Appl. No. 16/163,828, Examiner Interview Summary dated Oct. 27, 2022", 2 pgs.

"U.S. Appl. No. 16/163,828, Notice of Allowance dated Jan. 25, 2023", 8 pgs.

"U.S. Appl. No. 16/163,828, PTO Response to Rule 312 Communication mailed Mar. 14, 2023", 2 pgs.

"U.S. Appl. No. 16/163,828, Response filed Nov. 2, 2022 to Non Final Office Action dated Aug. 10, 2022", 6 pgs.

"Australian Application Serial No. 2019360094, Voluntary Amendment filed Apr. 13, 2021", 16 pgs.

"European Application Serial No. 19798770.4, Response filed Jan. 2, 2023 to Communication Pursuant to Article 94(3) EPC dated Jul. 4, 2022", 8 pgs.

"Japanese Application Serial No. 2021-521125, Voluntary Amendment filed Oct. 11, 2022", w/English Claims, 11 pgs.

"U.S. Appl. No. 16/163,828, Advisory Action dated Jun. 6, 2022", 3 pgs.

"U.S. Appl. No. 16/163,828, Non Final Office Action dated Aug. 10, 2022", 8 pgs.

"U.S. Appl. No. 16/163,828, Response filed May 23, 2022 to Final Office Action dated Apr. 4, 2022", 8 pgs.

"U.S. Appl. No. 16/163,828, Response filed Jul. 5, 2022 to Advisory Action dated Jun. 6, 2022", 8 pgs.

"European Application Serial No. 19798770.4, Communication Pursuant to Article 94(3) EPC dated Jul. 4, 2022", 5 pgs.

"European Application Serial No. 19798770.4, Response filed Apr. 14, 2022 to Notification to Correct Deficiency in the Amendments Rule 137(4) dated Mar. 18, 2022", w/o Claims, 2 pgs.

"Japanese Application Serial No. 2021-521125, Office Action dated Jul. 4, 2023", w/ English Translation, 9 pgs.

* cited by examiner

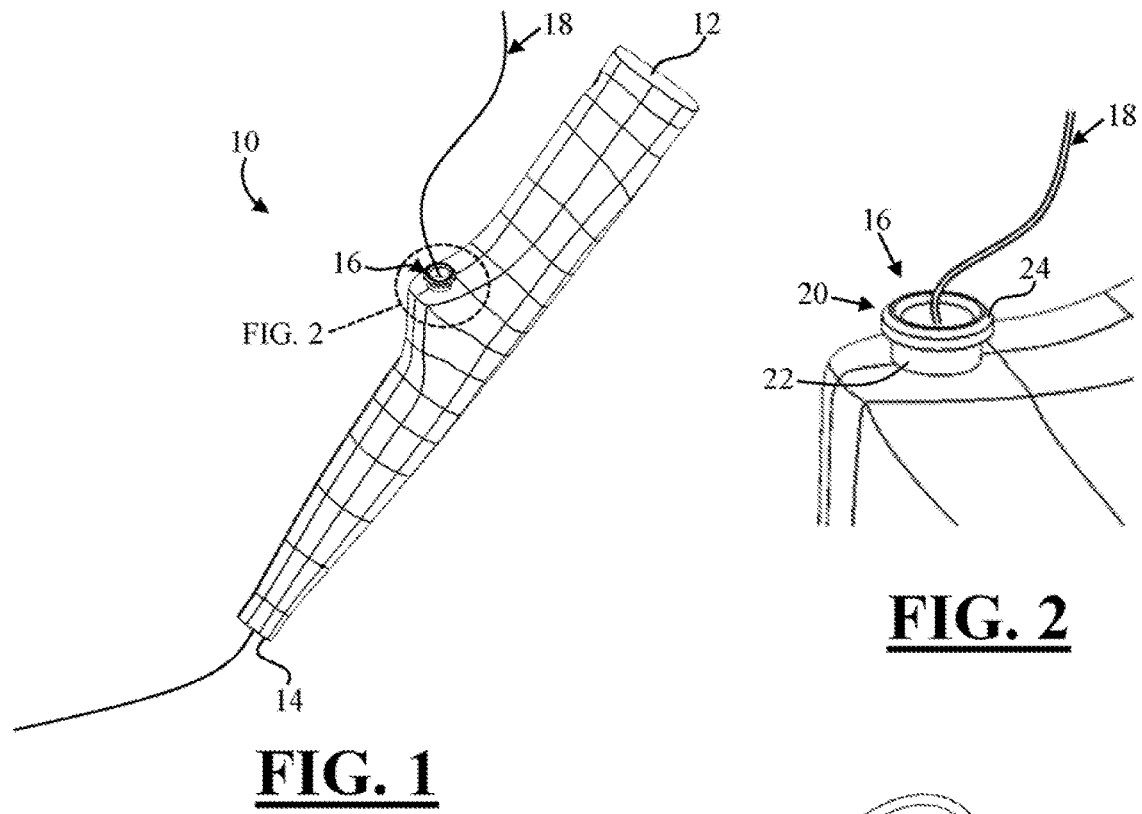
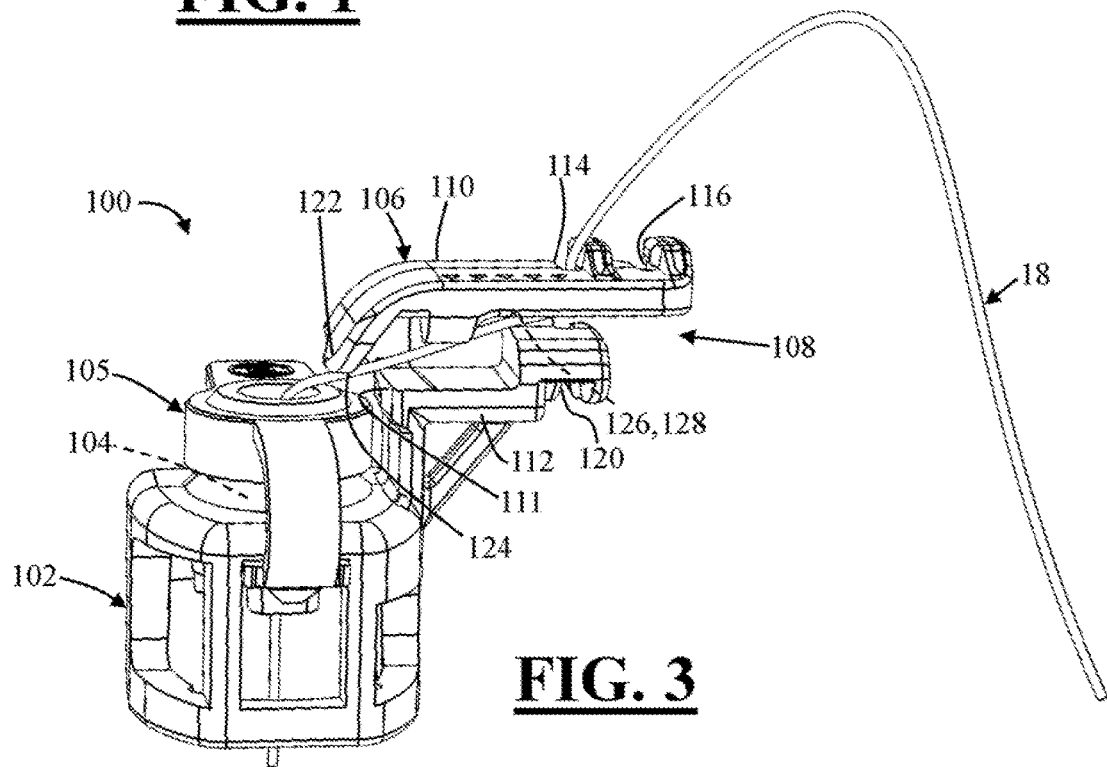

GUIDEWIRE LOCKING DEVICE

FIELD

These teachings relate to a medical device, and more particularly to a guidewire locking device having one or more features for guiding and/or restricting or preventing movement of a guidewire.

BACKGROUND

Endoscopes may be used in various medical procedures to access areas of the anatomy that are difficult to visualize and/or that may otherwise require an open procedure to access.

A guidewire is a long and relatively flexible wire that can be navigated through passageways in the anatomy. During a medical procedure, a guidewire may be passed through a working channel of the endoscope and then navigated to a site of interest in the anatomy. After the guidewire has reached the site of interest, manually holding and maintaining the long and flexible guidewire in a stationary position at the site of interest can be cumbersome.

During some medical procedures, a plurality of guidewires and/or medical instruments can be present at the surgical site. Manipulating one or more guidewires and/or medical instruments while maintaining other guidewires in a stationary position may be cumbersome. Moreover, manipulating one or more guidewires and/or medical instruments may cause one or more other guidewires to inadvertently move or become dislodged from the site of interest, which may cause patient trauma, frustrate a physician, and/or unnecessarily prolong a medical procedure.

Some devices have been previously proposed to help stabilize and/or maintain guidewires in a stationary position, such as those disclosed in US 2004/0162465, U.S. Pat. No. 7,637,863, and 6,893,393, which are all hereby incorporated by reference herein for all purposes.

However, at least some of the available devices are difficult or cumbersome to operate.

Moreover, some of the available devices are unable to prevent a wire loop from forming. A wire loop may form in an area between or adjacent the endoscope and a wire locking feature, particularly in an area where the guidewire is bent. A wire loop may cause the distal end of the guidewire to unintendedly move, shift, or become dislodged from a site of interest in the anatomy, which may cause patient trauma, frustrate a physician, and/or prolong a medical procedure.

In view of at least the foregoing, improvements in the art may be desirable.

SUMMARY

These teachings provide a device which addresses at least some of the needs discussed above.

These teachings provide a device that has a body, a channel, and a wire locking feature. The body has an opening through which a wire is configured to extend. The channel is defined by an upper wire guiding portion and a lower wire guiding portion. The wire locking feature is configured to immobilize a section of the wire or restrict or inhibit movement of the wire. The channel is configured to guide the wire along a path between the body and the wire locking feature.

These teachings provide a device that has a body. The body has an opening through which a wire is configured to extend. The device has a wire guide has a channel defined by an upper wire guiding portion, an opposing lower wire guiding portion. A section of the wire is configured to be routed into the channel. The wire guide comprises a first wire contacting feature that is configured to contact the wire at a first location. The first location is distal of the section of the wire that is routed into the channel.

These teachings provide a device that has a body, a channel, and a wire locking feature. The body has an opening through which a wire is configured to extend. The channel is defined by an upper wire guiding portion and a lower wire guiding portion. The channel is configured to guide the wire between the opening and the wire locking feature. The upper wire guiding portion comprising a protrusion. The wire is configured to slip past the protrusion during insertion of the wire into the channel.

These teachings provide a method including a step of routing a wire through a channel between a medical device and a wire locking feature. Prior to the routing step, the wire is passed under a protrusion.

BRIEF DESCRIPTION OF THE DRAWINGS

FIG. 1 is a perspective view of a medical device.
FIG. 2 is a close-up perspective view of an access port of the medical device of FIG. 1.
FIG. 3 is a perspective view of a wire locking device for sure with the medical device of FIG. 1.

DETAILED DESCRIPTION

Figure 4:
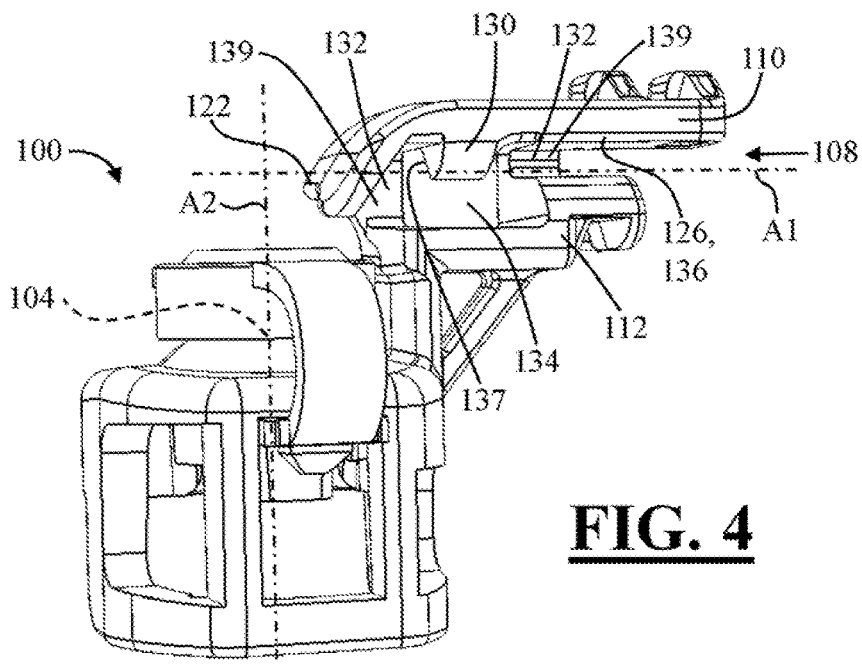
FIG. 4 is a perspective view of the wire locking device.

These teachings provide a medical device. The medical device may any device through which one or more wires or medical instruments can be passed. The medical device may be an endoscope. The medical device may be a bronchoscope, colonoscope, esophagoscope, or any other type of endoscope.

The medical device may include one or more internal channels or passageways into which or through which one or more wires or other medical instruments may be configured to pass. Water, air, suction, medicaments, or a combination thereof may be passed through the one or more channels or passageways of the medical device.

The medical device includes one or more access ports, providing access into the one or more channels or passageways of the medical device. The one or more access ports have one or more openings into which or through which one or more wires, medical instruments, or both can be inserted or removed from the medial device. A wire locking device according to these teachings may be configured to engage each access port of the medical device.

These teachings provide a wire locking device. The wire locking device may function to maintain one or more guidewires (also referred to herein as "wires"), or one or more other medical instruments, in a locked or stationary position relative to a medical device, an endoscope, a patient, anatomy, site of interest, or a combination thereof. A locked or stationary position means that the one or more wires or medical instruments are inhibited, restricted, or prevented from moving axially, laterally, rotationally, or a combination thereof. The wire locking device may function to lock or prevent movement of one or more wires, while a physician moves or manipulates another wire or other medical instrument without risk that the one or more wires may unintentionally move or slip. The wire locking device may function to restrict or prevent, or reduce or eliminate chances of, the one or more of the wires from forming loops or bends in a location between the medical device and the one or more wire locking features. A loop that is formed may function to cause the distal end of the one or more wires to move or be repositioned relative to a site of interest.

The wire locking device may engage or connect to any portion of a medical device, including an access port. The wire locking device may engage the medical device or the access port via snap fit, friction fit, adhesive, mechanical fastener, or a combination thereof.

The wire locking device may be a single-use device meaning the device is intended to be disposed after a single use. Alternatively, the wire locking device may be used in more than one medical procedure, and thus the wire locking device may be autoclavable.

The wire locking device may comprise one or more channels. The one or more channels may function to guide the one or more wires or medical instruments from the medical device to the wire locking features. The channel may function to provide a passageway, route, path, or area for the one or more wires to pass through between the medical device and the wire locking feature. The channel may function to contact one or more portions of the one or more wires and apply a friction force thereon to restrict or reduce movement (e.g., axial and/or rotational) of the one or more wires within the channel. The channel may function to contact the one or more wires in one or more areas of the wire that may be prone to form loops, for example, in areas where the wire is bent or turned, and thus reduce or eliminate chances of loops forming in those areas.

The channel may be defined by one or more portions or surfaces. For example, the channel may be generally rectangular or oval cross section. For example, the channel may be defined by one or more portions or surfaces may include: an upper wire guiding portion or surface, an opposing lower wire guiding portion or surface, one or more side walls or protrusions, or a combination thereof.

The channel, or the one or more portions or surfaces thereof, may be substantially smooth and/or have a low coefficient of friction to allow the one or more wires to easily slide thereon when routing the wires through the channel to the one or more wire locking features.

The channel, or one or more portions or surfaces thereof, may include one or more bumps, numbs, or friction areas with a higher coefficient of friction that may function to add or apply friction or resistance onto the one or more wires to slow, reduce, or restrict movement of the one or more wires within the channel. This may function to slow a wire from moving if the wire becomes separated or dislodged from the wire locking feature.

If the device comprises two or more channels, the channels may be provided on top of one another.

The wire guiding device may include one or more wire contacting features. A wire contacting feature may function to contact, move, bias, apply a pressure, force, or friction onto, change a direction of, reroute, or a combination thereof, one or more sections or portions of the one or more wires.

The one or more wire contacting features may function to contact and/or support the one or more wires in one or more areas where the one or more wires are bent or change direction to reduce or prevent the one or more wires from forming a loop in those areas. For example, if a wire is secured at a proximal end thereof, for example via the one or more wire locking features, and the wire is bent or turned and does not include a wire contacting feature at the bend or turn location, the wire may shift or snap and then form a loop at the bend or turn location, which may function to unintentionally cause a position of the distal end of the wire to move relative to the site of interest.

The wire contacting feature may be substantially smooth to allow the one or more wires to move or slide there along, or the wire contacting surface may include one or more bumps, numbs, or friction areas that may function to add or apply friction onto the one or more wires to restrict or reduce movement of the one or more wires there along.

A wire contacting feature may be any portion, section, or area of the channel. A wire contacting feature may be any inside surface of the walls or features defining the channel. For example, a wire contacting feature may be an inside surface or ceiling of the upper wire guiding portion, an inside surface or floor of the lower wire guiding portion, the one or more walls or protrusion, or a combination thereof.

An end of the wire guiding device may include a sloped surface or finger that slopes in a direction of the body or opening in the body. The sloped surface or finger may be a wire contacting surface. An angle of the slope of the finger may be sufficient to apply a force onto the one or more wires to distort or bend the wire into the channel and restrict or prevent a loop from forming at the bend location. The finger or sloped surface may contact and bend or support a wire bend at location before the wire enters the channel.

The wire guiding device may include one or more wire locking features. The wire locking feature may be any feature on the wire locking device that functions to restrict or prevent one or more of the wires from moving. That is, after the one or more wires engage one of the wire locking features, the wire is locked and substantially prevented from moving axially, rotationally, or both. In other words, the wire locking feature functions to lock the wire in a desired, predetermined position so that a distal end of the wire does not move relative to the site of interest.

The wire guiding device may include any number of wire locking features. For example, the upper wire guiding portion may include zero wire locking features, one or more wire locking features, two or more wire locking features, three or more features, etc. For example, the lower wire guiding portion may include zero wire locking features, one or more wire locking features, two or more wire locking features, three or more features, etc.

Each of the wire locking features may include a slot or channel, a well, and an undercut or tapered section. The features cooperate to hold the wire in place. The wire can be inserted into a slot, which may have a lead in or wide opening to make it easier to route the wire therein. The channel may narrow or taper inwardly from the opening to an undercut or tapered section. The wire may need to be forced past the undercut or tapered section to enter the well. After the wire is forced past the undercut or tapered section, the wire may snap into the well, which may make an audible click sound or vibration, advising the physician that the wire is engaged in the well. The undercut or tapered section may function to hold the wire in the well and prevent the wire from coming out of the well. In order to remove the wire from within the well, the wire may be required to be forced out of the well past the undercut or tapered section. This may function to reduce or prevent chances of the wire coming out of the well prematurely or unintendedly.

A slot of a wire locking feature on the upper wire guiding portion may be substantially aligned along an axis with a slot of a wire locking feature on the lower wire guiding portion. Alternatively, the slots of on the opposing guiding features need not be aligned but may instead be offset relative to one another.

The wire guiding device may include one or more caps. The cap may be a biopsy cap. The cap may be a cover, seal, or lid that functions to close off the opening into the access port or medical device. The cap may function to restrict or prevent foreign objects or matter from entering the inside of the access port or medical device. The cap may function to restrict or prevent spilling of bodily fluids from the access port. The cap may function to form a fluid and/or air barrier into the working channel of the medical device.

The cap may be integrally formed with or onto the body, or may be removably attached thereon. The cap may include an opening that is substantially aligned with the opening defined in the body and/or the opening of the access port on the medical device. The opening in the cap may confirm to the one or more wires extending through the cap to restrict or prevent foreign objects or matter from entering the inside of the access port or medical device. That is, the opening in the cap may expand when more than one wire is pass therethrough, and may collapse when only one wire is passed therethrough.

The cap may be made of a rubber or polymeric material. The cap may be made of a soft, pliable material. The cap may be made of a rigid plastic material. The cap may be made of a same material as the body. The cap may be made of a different material than the body.

One or more wires or other medical devices or instruments may be passed through the medical device, the wire locking device, or both. The one or more wires may be long, slender, and relatively flexible members that may be used to gain and maintain access in the body's narrow passageways during a medical procedure that may be minimally invasive, or not.

FIG. 1 illustrates a medical device 10. The medical device 10 may any device through which one or more wires, guidewires, and/or medical instruments can be passed. The medical device 10 may be an endoscope.

The medical device 10 comprises a proximal end 12 and an opposing distal end 14. The medical device 10 comprises an opening, port, or an access port 16 through which a guidewire 18, or a wire for short, two or more wires, and/or other medical instrument(s) may be provided into a channel or passageway defined inside the medical device 10. The wire(s) 18 may be guided or navigated distally through the channel or passageway of the medical device 10 and then extend out of the medial device 10 through an opening defined in the distal end 14 thereof. The one or more wires 18 or instruments may be guided or navigated from the medical device 10 to a site of interest in the anatomy.

FIG. 2 illustrates the access port 16 of the medical device 10 of FIG. 1. The access port 16 provides access into the passageway defined inside the medical device 10. The access port 16 comprises a flare 20. The flare has a base 22 connected to medical instrument 10, and a ring 24 attached to an upper portion of the base 22. The ring 24 has a size or diameter that is larger than, or flared outwardly from, the base 22. As will be discussed further below, a wire locking device 100 FIG. 3 is configured to contact, engage, and/or connect to the access port 16 of the medical device 10. One or more guidewires 18, wires, or other medical instruments are configured to pass through an opening of the access port 16 and into one or more channels or passageway defined within the medical device 10 and then out of the distal end 14 of the device 10 (FIG. 1).

FIG. 3 illustrates a wire locking device 100. The device 100 comprises a body 102. The body 102 has an opening 104 through which one or more wires 18 are configured to extend. A cap or cover 105 is attached to the body 102. The cap 105 also has an opening through which the one or more wires 18 are configured to extend. By having the cap 105 that is part of, connected to, or made integral with the device 100 or body 102, a geometry of the wire 18 can be controlled and consistently routed between the medical device 10 and the wire locking device 100. That is, wire curves or bends can be better controlled as the wire 18 extends between the opening 104 and a wire guide 106 discussed further below, which may advantageously reduce wire loops from forming.

The wire locking device 100 comprises a wire guide 106, which may also be referred to as an arm, that is located adjacent to the body 102. The wire guide 106 or arm comprises a channel 108 that is defined by an upper wire guiding portion 110 and an opposing lower wire guiding portion 112. The channel 108 is configured to guide the one or more wires 18 along a path between the body 102 and one or more wire locking features that are configured to engage and immobilize a section of the wire 18 when the wire 18 is routed into the corresponding wire locking feature, discussed further below.

The wire locking features include: a first wire locking feature 114 and a second wire locking feature 116, both of which are located on the upper wire guiding portion 110, and a wire locking feature 120 located on the lower wire guiding portion 112. These features 116, 118, 120 are illustrated in greater detail in FIGS. 6-9 and 14-15.

The upper wire guiding portion 110 comprises a first wire contacting feature 122 that is configured to contact the wire 18 at a first location 124. The first wire contacting feature 122 extends beyond a leading edge 111 of the lower wire guiding portion 112 and the channel 108, and thus the first wire contacting feature 122 is configured to contact a portion of the wire 18 that is distally located relative to the section of the wire 18 that is located in side of the channel 108.

The first wire contacting feature 122 is a finger comprising a sloped surface that slopes or is angled downwardly in a direction of the opening 104. The first wire contacting feature 122 or finger is located laterally above the opening 104. The first wire contacting feature 122 can also be seen in FIGS. 4, 5, 6, 8.

Figure 5:
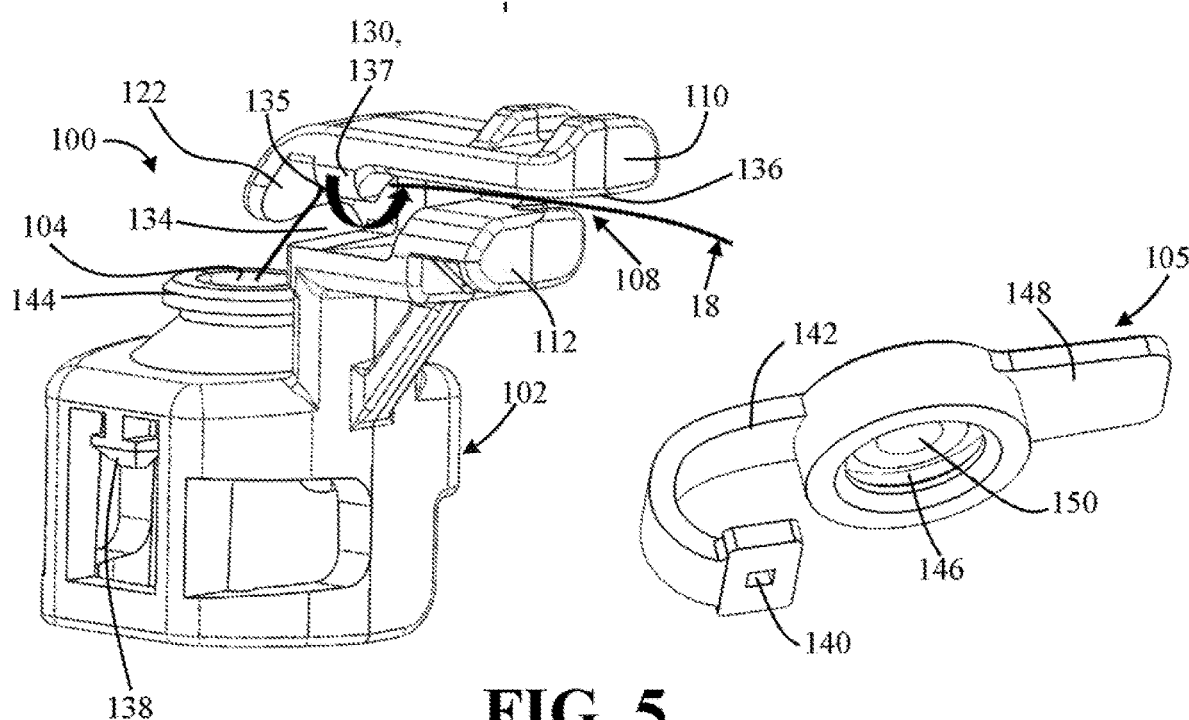
FIG. 5 is an exploded, perspective view of the wire locking device.

The upper wire guiding portion 110 comprises a second wire contacting feature 126 that is configured to contact the wire 18 at a second location 128. The second wire contacting feature 126 may be a ceiling 136 of the upper wire guiding portion 110 (FIGS. 4 and 5). The second wire contacting feature 136 may be an inside surface of one or both of the side walls 130, 132 defining the channel 108 (FIGS. 4 and 5). The second wire contacting feature 126 is configured to contact the wire 18 at a location proximal to the location on the wire 18 where the first wire contacting feature 122 is configured to contact the wire 18.

The first and second wire contacting features 122, 124 may function as a support, stop, restraint, or boundary to limit vertical, horizontal, and/or lateral motion of the wire 18 as the wire 18 extends from the opening 104 to one or more of the wires locking features 116, 118, 120. Stated another way, the one or more wires 18 may form one or more loops in places where the wire 18 is bent, turned, or changes direction. By having the wire contacting features 122, 124 supporting or contacting the wires 18 in these areas where the wire 18 may bend, turn, or change directions, loops are restricted or prevented from forming. If a wire loop is formed, the wire 18 may be unintendedly pulled from inside the patient or site of interest in the anatomy, which may undesirably result in the wire 18 losing its position inside the anatomy. Therefore, preventing such wire loops from forming is desirable. Moreover, the wire contacting features 122, 124 are configured to apply a frictional force onto the wire 18, which functions to add resistance to the wire 18 thereby reducing or preventing the wire 18 from axially, laterally, or rotationally moving.

FIG. 4 illustrates the wire locking device 100 with the wire 18 removed for clarity. The channel 108 extends along a longitudinal axis A1 that is generally and/or substantially perpendicular to an axis A2 that the opening 104 extends along.

In addition to the upper wire guiding portion 110 and the opposing lower wire guiding portion 112 defining the channel 108, the channel 108 also includes opposing side walls 130, 132. The walls 130, 132 are configured to laterally maintain the one or more wires 18 within the channel 108 after the wire(s) 18 have been routed therein. The walls 130, 132 may be generally vertical walls relative to the upper and lower wire guiding portions 110, 112. The walls 130, 132 may be angled relative to the upper and lower wire guiding portions 110, 112.

Side wall 130, which may also be referred to as a protrusion, extends downwardly from the upper wire guiding portion 110 towards the lower wire guiding portion 112, but does not contact the lower wire guiding portion 112. A gap 134 is defined between the lower end of the side wall or protrusion 130 and the lower wire guiding portion 112.

In some configurations, the protrusion or side wall 130 may instead extend upwardly from the lower wire guiding portion 112 towards the upper wire guiding portion 110. In such a configuration, the gap 134 would be defined between the end of the side wall or protrusion 130 and the upper wire guiding portion 110.

While a gap or cut out is shown between the two sections or portions defining sidewall 132, the gap or cutout may be eliminated to have a single, integral, continuous wall 132.

FIG. 4 also illustrates the second wire contacting feature 126, which may be any portion of the ceiling 136 of the upper wire guiding portion 110. Additionally, or alternatively, the second wire contacting feature 126 may be one or both of the inside surfaces 137, 139 of the side walls 130, 132 facing the inside of the channel 108. The inside surface 137 of protrusion 130 is a generally flat and planar surface (See also FIG. 5)

FIG. 5 illustrates the device 100, with the cap 105 separated from the body 102. The protrusion 130 has a rounded outside surface 137 that faces away from an inside of the channel 108. The wire 18 can be inserted into the channel 108 by pressing the wire 18 against the rounded surface 137 and then applying a slightly downwardly force so that the wire 18 slides downwardly along the rounded surface 137 and then into the channel 108 along path 135. As the wire 18 slides into the channel 108, the wire 18 may then snap upwardly and contact the ceiling 136 of the upper wire guiding portion 110. The snap may be caused by the wire 18 building up potential energy in a manner similar to a spring, and then suddenly converting the potential energy to kinetic energy as the wire is bent down around the protrusion 130 and then allowed to straighten after the wire 18 is include the channel 108. The contact of the wire 18 against the ceiling 136 (and/or against the side walls 130, 132 and/or bottom surface of the bottom wire guiding portion 112) may produce or generate an audible click sound and/or vibration, which may provide a tactical feedback of the wire 18 being located into the channel 18.

Additionally, or alternatively, the wire 18 can be inserted into the channel 108 by aligning the wire 18 with the gap 134 defined between the upper wire guiding portion 110 and the opposing lower wire guiding portion 112 and then pressing or pushing the wire 18 into the channel 108.

The body 102 comprises an attachment feature 138 that is configured to cooperate with an opening 140 defined in a tether or strap 142 of the cap 105. This may advantageously allow or provide for the cap 105 to be removed from the body 102 for cleaning and/or replacement if the cap 105 becomes dirty, damaged or worn. In some configurations, the attachment between the body 102 and the cap 105 can be permanent so that the cap 105 cannot be separated from the body 102 without damaging either or both of the cap 105 and body 102.

The body 102 comprises a flare 144 defined around opening 104. The flare 144 is configured to cooperate with a corresponding flare engaging feature 146 defined on an underside of the cap 105 to connect the cap 105 to the body 102. The features 144, 146 cooperate to form an interference fit for the cap 105 to stay attached to the body 102 during handling of the medical device 10. The cap 105 includes a pull tab 148. The pull tab 148 can be lifted by a user to aid in removing the cap 105 from the body 102. The cap 105 comprises an opening 150 that is generally aligned with the opening 104 in the body 102 for the wire(s) 18 to pass through the cap 105.

Figure 6:
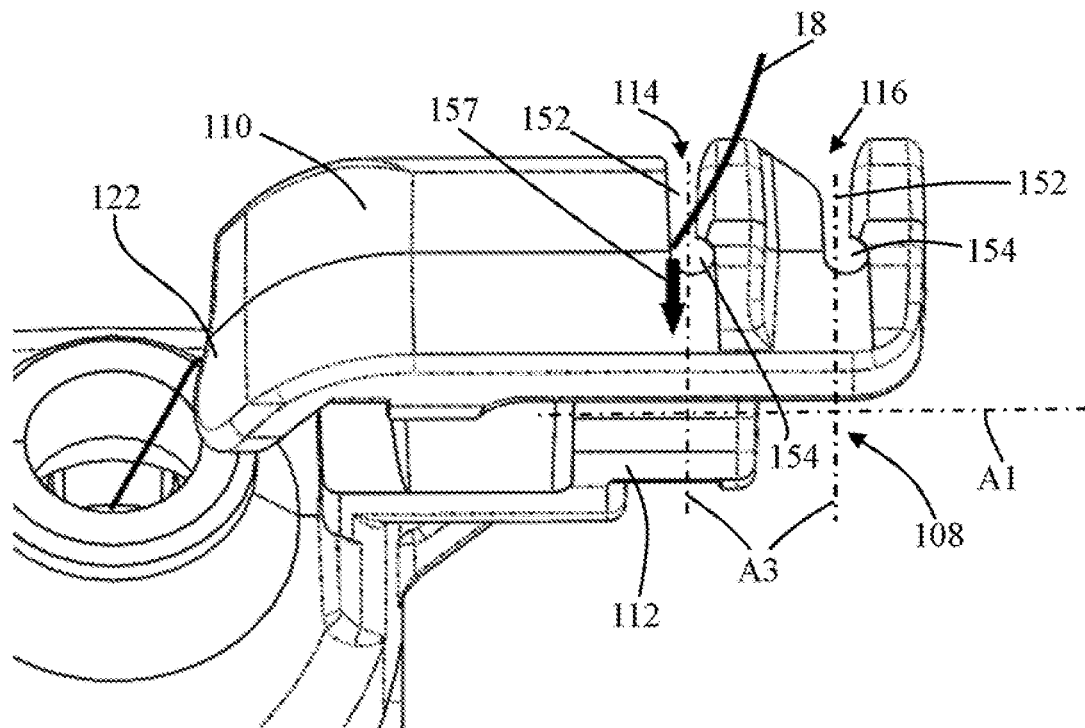
FIG. 6 is a partial perspective view of the wire locking device.

FIG. 6 illustrates a portion of the upper wire guiding portion 110, showing the first and second wire locking features 114, 116. While the wire locking feature 120 on the lower wire guiding portion 112 is not shown in this figure, its structure and function is substantially similar to that of the first and second wire locking features 114, 116. Accordingly, the description of structure and function of the first and second wire locking features 114, 116 may be applicable to the structure and function of the wire locking feature 120.

Each of the first and second wire locking features 114, 116 comprises a slot 152 and a well 154. Each slot 152 extends along a corresponding axis A3 that is substantially perpendicular to the axis A1 that the channel 108 extends along. Each slot 152 tapers inwardly from an open end to the corresponding well 154.

Figure 7:
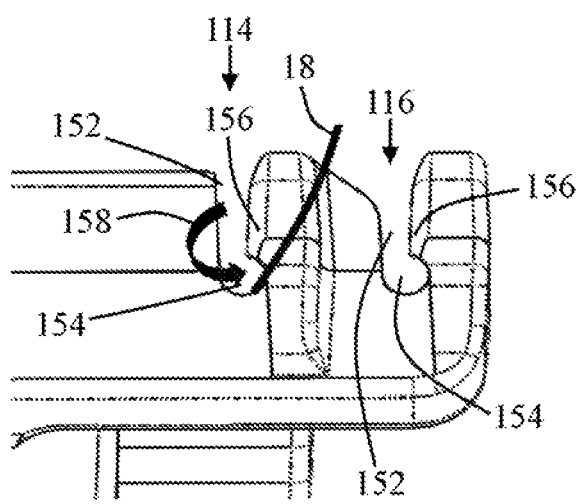
FIG. 7 is a partial perspective view of the wire locking device.

With additional reference to FIG. 7, each slot 152 comprises a tapered wall 156 or undercut located adjacent the well 154 that tapers inwardly towards the center axis A3 of the slot 152. The well 154 has a larger size or diameter than the tapered section 156. To engage the wire 18 inside the wire locking features 114, 116, 120 to restrict, prevent, or inhibit movement of the wire 18, the wire 18 can be inserted into the corresponding channel 152 in direction 157 (FIG.

6), bent around the corresponding tapered wall 156 or undercut in direction 158 (FIG. 7), and then snapped into the corresponding well 154. Potential energy stored in the wire 18 may be released as the wire 18 is bent around the tapered section 156 and snapped into the well 154, which may generate or produce an audible click sound and/or vibration, which may provide a tactical feedback of the wire 18 being engaged in the wire locking feature 114, 116, 120.

Figure 8:
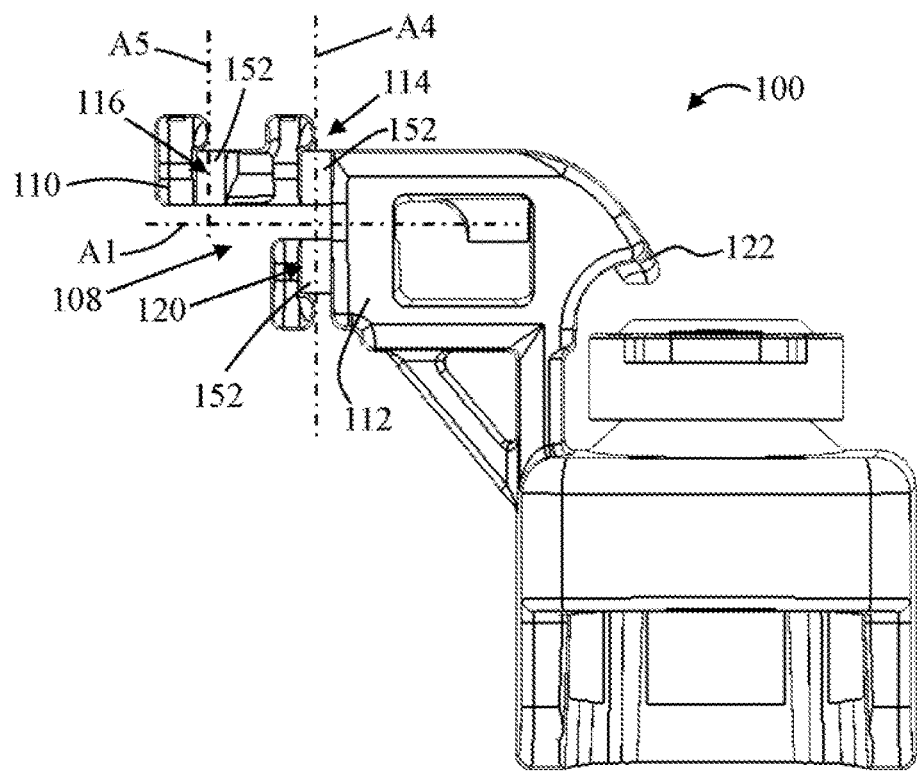
FIG. 8 is a back view of the wire locking device.

Referring to FIG. 8, the channel 152 of the wire locking feature 114 on the upper wire guiding portion 110 and the channel 152 of the wire locking feature 120 on the lower wire guiding portion 112 and are substantially and/or generally aligned on a common axis A4, which is substantially and/or generally perpendicular to the axis A1 of the channel 108. Channel 152 of wire locking feature 116 extends along an axis A5 that is substantially and/or generally parallel to axis A4 and generally and/or substantially perpendicular to axis A1.

Figure 9:
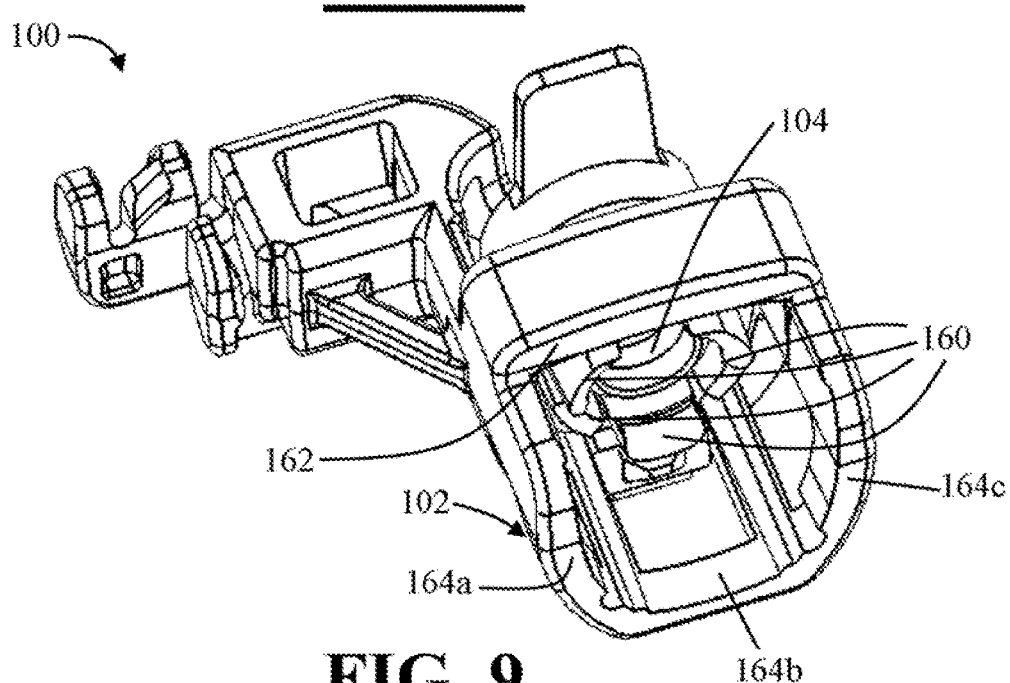
FIG. 9 is a perspective view of a bottom of the wire locking device.

Referring now to FIG. 9, the body 102 comprises one or more snap fit features or fingers 160. The body 102 comprises an edge 162 and a skirt comprising three walls or surfaces 164a, 164b, 164c surrounding the opening 104. The device 100 is free of a skirt surface on the edge 162. The skirt surfaces 164a, 164b, 164c extend downwardly from the opening 104 and are longer than the edge 162.

Preferably, the body 102 comprises three snap fit features or fingers 160 that are spaced equally around the opening 104. However, in some configurations, the body 102 may have less than three snap fit features or fingers 160, or more than three snap fit features or fingers. In some configurations, the snap fit features or fingers 160 may be unequally spaced around the opening 104.

The snap fit features or fingers 160 are configured to be at least partially biasable, flexible, and/or resilient, and are configured to at least partially deflect outwardly away from the center opening 104 when the wire locking device 100 initially contacts or engages the access port 16 of the medical device 10 (FIGS. 1-2, 10) during installation of the wire locking device 100 onto the medical device 10.

The snap fit features or fingers 160 are also configured to deflect outwardly away from the center opening 104 when the wire locking device 100 begins to be removed or separated from the access port 16 of the medical device 10 (FIGS. 1-2, 11) so that the wire locking device 100 can be separated from the medical device 10.

Figure 10:
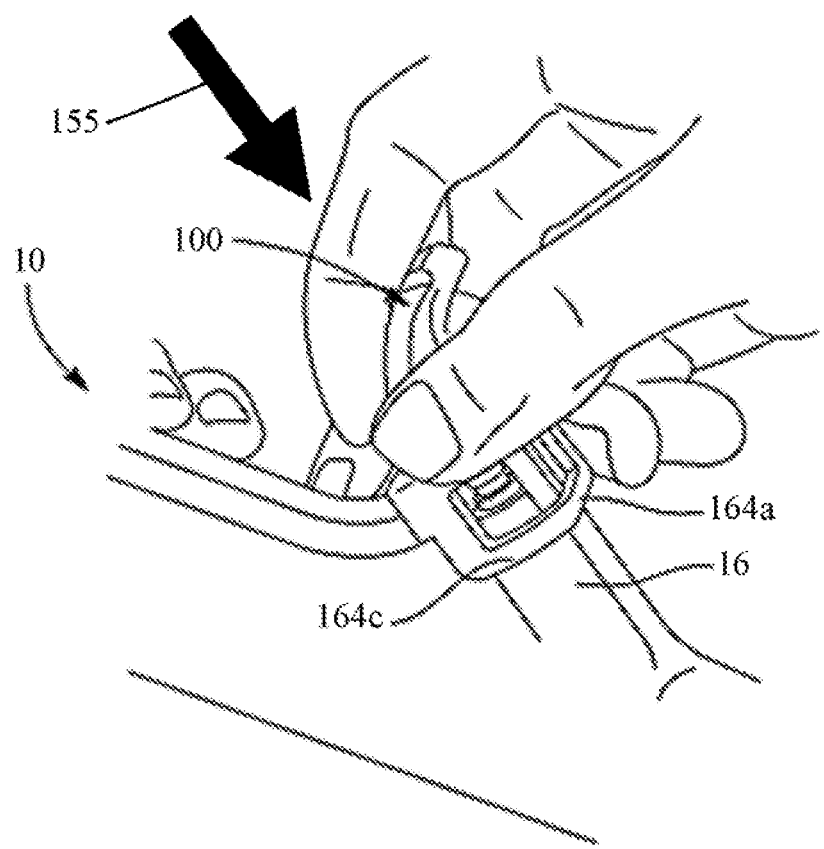
FIG. 10 is a perspective view of the wire locking device being installed onto the medical device.

With additional reference to FIGS. 1, 2, and 10, the wire locking device 100 can be installed onto the medical device 10 according to a method. The method may include one or more of the steps disclosed herein. The wire locking device 100 can be attached or installed on the device 10 by aligning the wire locking device 100 with the access port 16 of the medical device 10. The wire locking device 100 may be aligned relative to the medical device 10 such that the skirt surfaces 164a, 164b, 164c and edge 162 surround the access port 16. The wire locking device 100 may then be moved downwardly in a direction 155 onto the access port 16 until the snap fit features or fingers 160 contact the ring 24. Continued downward movement of the device 100 onto the access port 16 in direction 155 causes the access port 16 to move or force the fingers 160 to spread outwardly away from the opening 104 to make room for the access port 16 to fit between the fingers 160.

Further downward movement of the wire locking device 100 onto the access port 16 eventually causes the fingers 160 to resiliently deflect or snap back inwardly towards the opening 104 into their steady state position. The fingers 160 may click or snap back against the base 22 and/or below ring 24, which may provide an audible click or tactical sound or vibration so the user knows the device 100 has been installed and is properly seated on the medical device 10.

The snap fit features or fingers 160 may have undercuts or tabs 166 (See FIGS. 12 and 13) that are configured to engage a bottom surface of the ring 24 to lock and maintain a connection of the wire locking device 100 on the access port 16 and the medical device 10. The skirt surfaces 164a, 164b, 164c surrounding the access port 16 may also function as an anti-rotation feature that is/are configured to restrict or prevent the wire locking device 100 from rotating relative to or about the access port 16.

Figure 11:
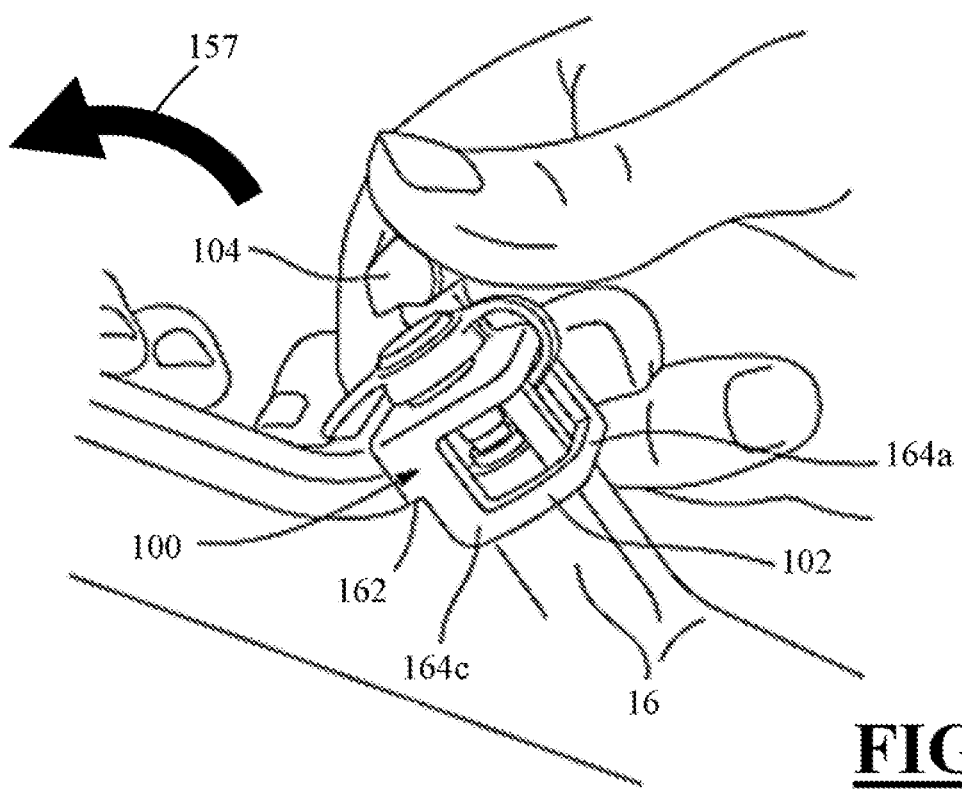
FIG. 11 is a perspective view of the wire locking device being removed or separated from the medical device.

Referring now to FIG. 11, to remove or separate the wire locking device 100 from the medical device 10, a user may grasp the wire locking device 100 and push or apply a rocking or pivoting force onto the body 102 or the arm or wire guide 106 in direction 157 so that the wire locking device 100 tips, rocks, or pivots on or about its edge 162 (See also FIG. 9) and then separated from the medical device 10.

Figure 12:
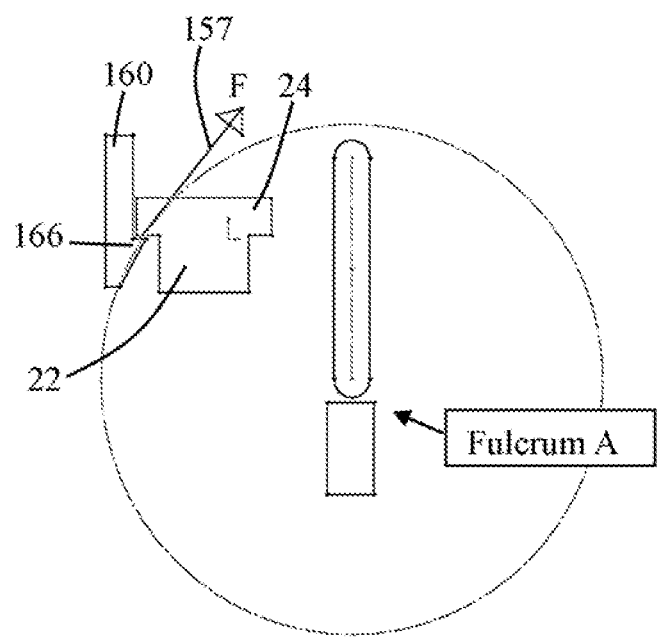
FIG. 12 is a schematic representation of a locking feature or finger of the wire locking device engaging the access port of the medical device.

With additional reference to FIG. 12, the force F applied onto the device 100 and/or the fingers 160 in direction 157 during this tipping, pushing, pivoting, and/or rocking motion will cause the fingers 160 to deflect and expand outwardly away from the opening 104 and each other so that the fingers 160 and under cut features 166 move away from the base 22 and clear enough space for the wire locking device 100 to disengage the ring 24 so that the wire locking device 100 can be separated from the medical device 10.

Figure 13:
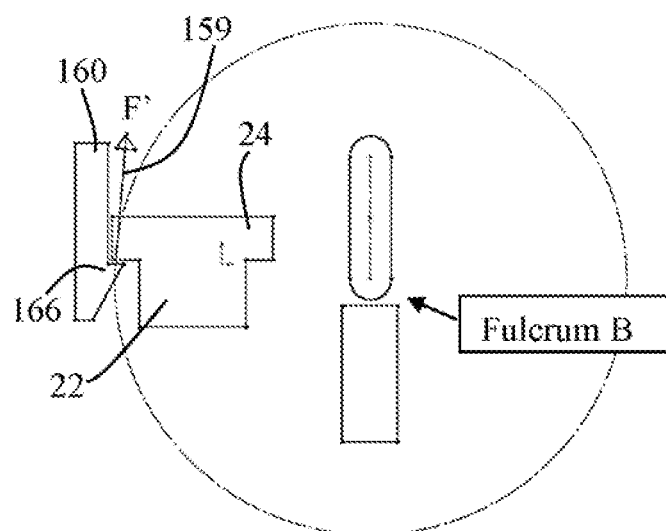
FIG. 13 is a schematic representation of a locking feature or finger of the wire locking device engaging the access port of the medical device.

In contrast, referring now to FIG. 13, if a force F' is applied onto the device 100 or finger 160 that is not directed towards the edge 162 (i.e., if the force F' is in direction 159 or is vertical and not a pushing force or an angled or rocking force towards edge 162 like in FIG. 12), the corresponding snap fit feature or finger 160 or undercut 166 will prevent the force F' from being delivered in an upward direction thereby restricting or preventing removal or separation of the wire locking device 100 from the medical device 10. Instead, the ring 24 of the access port 16 will be pressed against one or more of the snap fit features or fingers 160 thereby increasing the grip of the wire locking device 100 on the medical device 10.

Figure 14:
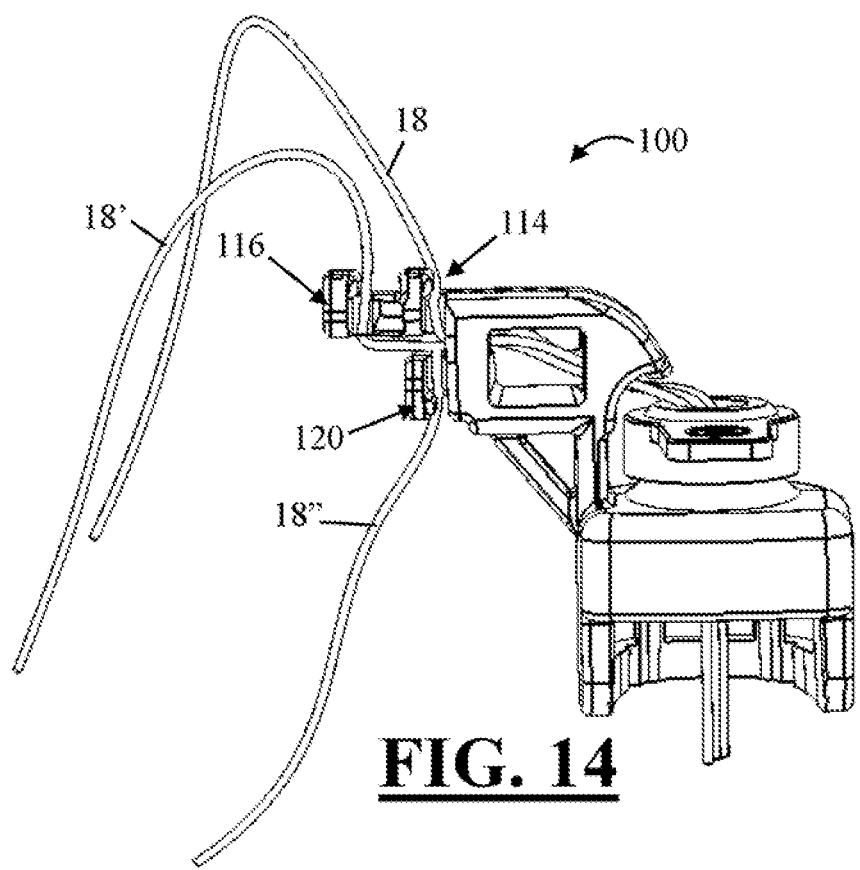
FIG. 14 is a perspective view of the wire locking device.
Figure 15:
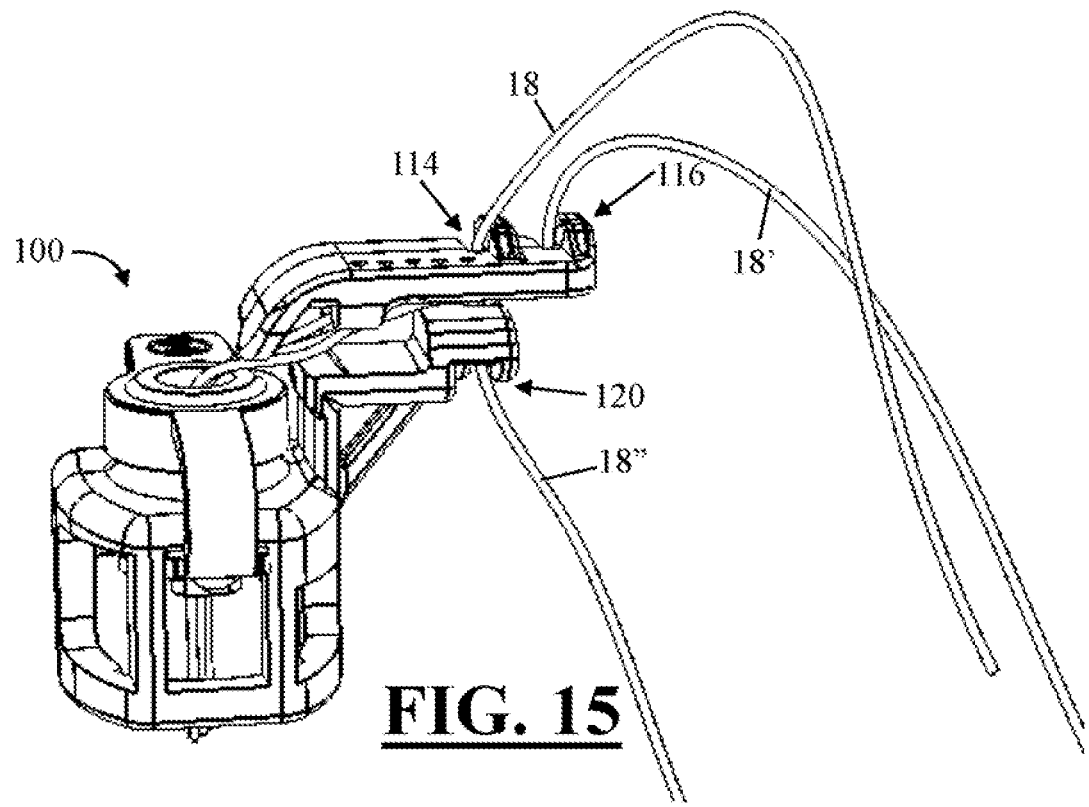
FIG. 15 is a perspective view of the wire locking device.

FIGS. 14 and 15 each illustrate the wire locking device 100 with three wires 18, 18', 18", each engaging a corresponding one of the wire locking features 114, 116, 120.

It is understood that the method steps disclosed herein can be performed in virtually any order. Moreover, one or more of the following method steps can be combined with other steps; can be omitted or eliminated; can be repeated; and/or can separated into individual or additional steps.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A device comprising:
   a body comprising an opening through which a wire is configured to extend;
   an upper wire guiding portion having a first side and a second side opposite the first side, the first side of the upper wire guiding portion facing a lower wire guiding portion parallel thereto, the upper wire guiding portion including at least one wire locking feature disposed on the second side of the upper wire guiding portion, the at least one wire locking feature extending from the second side of the upper wire guiding portion and away from the lower wire guiding portion;
   a channel extending along the upper wire guiding portion, the channel configured to guide the wire between the opening and the at least one wire locking feature; and
   a protrusion extending from the upper wire guiding portion toward the lower wire guiding portion, the protrusion configured to contact the wire to bias the wire toward the channel.

2. The device according to claim 1, wherein the protrusion comprises a rounded surface along which the wire is configured to slide during insertion of the wire into the channel.

3. The device according to claim 2, wherein the rounded surface faces away from an inside of the channel.

4. The device according to claim 1, wherein the at least one wire locking feature extends through the upper wire guiding portion, and wherein the at least one wire locking feature comprises a slot and a well.

5. The device according to claim 4, wherein the slot extends along a center axis that is generally perpendicular to a longitudinal axis of the channel.

6. The device according to claim 4, wherein the slot has an open end and a tapered section, and the well is adjacent the tapered section.

7. The device according to claim 6, wherein the well is larger than the tapered section of the slot.

8. The device according to claim 1, wherein the at least one wire locking feature is located on the upper wire guiding portion.

9. The device according to claim 8, wherein another wire locking feature is located on the lower wire guiding portion.

10. The device according to claim 9, wherein a slot of the at least one wire locking feature on the upper wire guiding portion is generally aligned with a slot of the wire locking feature on the lower wire guiding portion.

11. The device according to claim 1, wherein the channel extends along an axis that is generally perpendicular to an axis that the opening extends along.

12. The device according to claim 11, wherein the wire locking feature comprises a slot that is generally perpendicular to a longitudinal axis of the channel.

13. The device according to claim 1, wherein the channel comprises opposing walls between which the wire is routed, wherein the opposing walls are configured to maintain the wire inside of the channel, and wherein the opposing walls are generally perpendicular to the upper wire guiding portion and the lower wire guiding portion.

14. A device comprising:
   a body comprising an opening through which a wire is configured to extend;
   an upper wire guiding portion and a lower wire guiding portion, the upper wire guiding portion including a proximal portion, a distal portion, a first side and a second side opposite the first side, wherein:
     at least the proximal portion extends parallel to the lower wire guiding portion and including at least one wire locking feature disposed on the second side of the upper wire guiding portion, the at least one wire locking feature extending from the second side of the upper wire guiding portion and away from the lower wire guiding portion; and
     the first side of the upper wire guiding portion faces the lower wire guiding portion;
   a channel extending along the upper wire guiding portion, the channel configured to guide the wire between the opening and the wire locking feature, wherein the distal portion of the upper wire guiding portion extends distally beyond the lower wire guiding portion to contact the wire;
   a wall extending from the upper wire guiding portion toward the lower wire guiding portion, the wall located distally to the lower wire guiding portion and configured to limit lateral translation of the wire; and
   a protrusion extending from the upper wire guiding portion toward the lower wire guiding portion, the protrusion located distally to the lower wire guiding portion and opposing the wall, the protrusion configured to contact the wire to bias the wire toward the channel and the wall.

* * * * *